(12) United States Patent
Ziesche et al.

(10) Patent No.: US 11,182,881 B2
(45) Date of Patent: Nov. 23, 2021

(54) DECONVOLUTION APPARATUS AND METHOD USING A LOCAL SIGNAL-TO-NOISE RATIO

(71) Applicant: LEICA MICROSYSTEMS CMS GMBH, Wetzlar (DE)

(72) Inventors: Florian Ziesche, Mannheim (DE); Kai Walter, Schriesheim (DE); Juergen Reymann, Heidelberg (DE)

(73) Assignee: LEICA MICROSYSTEMS CMS GMBH, Wetzlar (DE)

( * ) Notice: Subject to any disclaimer, the term of this patent is extended or adjusted under 35 U.S.C. 154(b) by 0 days.

(21) Appl. No.: 17/273,743

(22) PCT Filed: Jan. 25, 2019

(86) PCT No.: PCT/EP2019/051863
§ 371 (c)(1),
(2) Date: Mar. 5, 2021

(87) PCT Pub. No.: WO2020/052814
PCT Pub. Date: Mar. 19, 2020

(65) Prior Publication Data
US 2021/0248720 A1    Aug. 12, 2021

(30) Foreign Application Priority Data

Sep. 14, 2018 (EP) ..................... 18194617

(51) Int. Cl.
*G06T 7/00* (2017.01)
*G06T 5/00* (2006.01)
(Continued)

(52) U.S. Cl.
CPC .............. *G06T 5/003* (2013.01); *A61B 1/043* (2013.01); *A61B 90/20* (2016.02); *G06T 5/002* (2013.01);
(Continued)

(58) Field of Classification Search
CPC ........... G06T 5/003; G06T 5/002; G06T 5/50; G06T 5/00; G06T 5/001; G06T 5/10;
(Continued)

(56) References Cited

U.S. PATENT DOCUMENTS 8,009,189 B2 * 8/2011 Ortyn ................... G02B 21/365
348/80
2003/0228065 A1    12/2003 Kaltschmidt
(Continued)

FOREIGN PATENT DOCUMENTS

DE        102 14 114 A1    10/2003
WO    WO 2014/074138 A1     5/2014

OTHER PUBLICATIONS

White, Richard L., "Image Restoration Using the Damped Richardson-Lucy Method", Proceedings of SPIE, vol. 2198, Jun. 1994 (Jun. 1994), pp. 1342-1348, XP055562456.
(Continued)

*Primary Examiner* — Jose L Couso
(74) *Attorney, Agent, or Firm* — Leydig, Voit & Mayer, Ltd.

(57) ABSTRACT

A method for a deconvolution of a digital input image ($I(x_i)$) having a plurality of input voxels ($x_i$), in particular a digital input image obtained from a medical observation device, such as a microscope or endoscope and/or using fluorescence, includes computing a local signal-to-noise ratio (SNR ($x_i$)) within an input region ($R(x_i)$) of the digital input image, the input region consisting of a subset of the plurality of input voxels of the digital input image and surrounding the current input voxel. A noise component ($\beta(SNR)$) is computed from the local signal-to-noise ratio, the noise component representing image noise ($n([h*f](x_i), n(x_i))$) in the deconvolution. The noise component is limited to a predetermined minimum noise value ($\beta_{min}$) for a local signal-to-noise ratio above a predetermined upper SNR threshold
(Continued)

value ($SNR_{max}$) and is limited to a predetermined maximum noise value ($\beta_{max}$) for a local signal-to-noise ratio below a predetermined lower SNR threshold value ($SNR_{min}$).

15 Claims, 3 Drawing Sheets

(51) Int. Cl.
*G06T 7/13* (2017.01)
*A61B 1/04* (2006.01)
*A61B 90/20* (2016.01)

(52) U.S. Cl.
CPC ...... *G06T 7/13* (2017.01); *G06T 2207/10056* (2013.01); *G06T 2207/10064* (2013.01); *G06T 2207/10068* (2013.01); *G06T 2207/20012* (2013.01)

(58) Field of Classification Search
CPC ....... G06T 7/13; G06T 7/0012; G06T 7/0004; G06T 2207/10056; G06T 2207/10068; G06T 2207/20012; G06T 2207/10064; G06T 2207/10061; G06T 2207/20201; G06T 2207/30024; G06T 2207/10121; G06T 2207/10052; G06T 2207/20221; G06T 2207/30004; G06T 2207/20056; G06T 2207/30028; G06T 2207/30092; G06T 2207/30096; G06T 2207/20182; G06T 2210/41; G06K 9/00127; G06K 9/00134; G06K 9/40; G06K 9/4628; G06K 9/00503; G06K 2209/403; H04N 2005/2255; H04N 9/646; G02B 21/365; G02B 21/16; G02B 21/0076; G02B 21/0088; G02B 21/34; G02B 21/002; G02B 21/0028; G01N 21/6458; G01N 21/6428; G01N 2201/12; G01N 2015/1445; A61B 1/043; A61B 1/00002; A61B 1/00004; A61B 1/00009; A61B 1/041; A61B 1/00; A61B 1/2736; A61B 90/20; A61B 90/361; A61B 3/13; A61B 3/135; A61B 3/12; A61B 5/0071; A61B 5/0059; A61B 5/0075; A61B 5/0084; A61B 5/7257; A61B 5/14556; A61B 2576/00

See application file for complete search history.

(56) References Cited

U.S. PATENT DOCUMENTS

| | | |
|---|---|---|
| 2005/0147313 A1 | 7/2005 | Gorinevsky |
| 2010/0074486 A1* | 3/2010 | Broser .................. G06T 7/0012 382/128 |
| 2011/0301438 A1* | 12/2011 | Sachse ................. A61B 5/0084 600/301 |
| 2012/0105655 A1 | 5/2012 | Ishii et al. |
| 2015/0119708 A1* | 4/2015 | Sachse ................. A61B 5/4887 600/431 |
| 2016/0180190 A1* | 6/2016 | Lifshin ................... H01J 37/28 382/201 |
| 2016/0266366 A1* | 9/2016 | Chung ................. G02B 21/008 |
| 2018/0143001 A1* | 5/2018 | Popescu ............... G02B 21/008 |
| 2018/0329225 A1* | 11/2018 | Kleckner ............ G06K 9/00127 |
| 2019/0180420 A1* | 6/2019 | Medina ..................... G06T 7/10 |
| 2020/0014983 A1* | 1/2020 | McRae ................. G01S 13/765 |
| 2020/0201018 A1* | 6/2020 | Vaziri .................. G02B 21/367 |

OTHER PUBLICATIONS

Laligant, O. et al. "Edge enhancement by local deconvolution", Pattern Recognition, Elsevier, GB, vol. 38, No. 5, May 2005 (May 2005), pp. 661-672, XP027610991.

Tapia, Ernesto, "A note on the computation of high-dimensional integral images," Pattern Recognition Letters 32 (2) (2011), pp. 197-201, Elsevier B.V., Oct. 27, 2010.

Fish, D.A. et al. "Blind deconvolution by means of the Richardson-Lucy algorithm," J. Opt. Soc. Am. A, vol. 12, No. 1, Jan. 1995.

Crow, Franklin C., "Summed-Area Tables for Texture Mapping," Computer Graphics, vol. 18, No. 3, ACM SIGGRAPH, pp. 207-212, Jul. 1984.

\* cited by examiner

DECONVOLUTION APPARATUS AND METHOD USING A LOCAL SIGNAL-TO-NOISE RATIO

CROSS-REFERENCE TO PRIOR APPLICATIONS

This application is a U.S. National Phase Application under 35 U.S.C. § 371 of International Application No. PCT/EP2019/051863, filed on Jan. 25, 2019, and claims benefit to European Patent Application No. EP 18194617.9, filed on Sep. 14, 2018. The International Application was published in English on Mar. 19, 2020 as WO 2020/052814 under PCT Article 21(2).

FIELD

The invention relates to a method and an apparatus for digital image restoration, in particular digital input images from microscopes or endoscopes.

BACKGROUND

In the area of image processing, deconvolution is known to enhance the resolution and reduce the noise in a digital input image. The underlying assumption of deconvolution is that the observed digital input image $I(x_i)$ results from the true image $\hat{f}(x_i)$ as follows:

$$I(x_i) = n\,([h*\hat{f}](x_i)) + n(x_i),$$

wherein $h(x_i)$ designates a linear transfer function, e.g. from the recording system, such as a point-spread function, $n(x_i)$ designates additive image noise, $n$ designates Poisson noise depending on the signal strength, $x_i$ designates an input voxel, and * denotes a convolution. In the deconvolution, i.e. the computation of an estimate of the true image $\hat{f}(x_i)$, the image noise is represented by a noise component.

The digital input image may be two or higher dimensional. Thus, put generally, the input image may be n-dimensional, n being an integer larger than one, n≥2.

At each input voxel $x_i$, the input image is represented by at least one image parameter I, a digital value, which in particular may be representative of light intensity. A voxel may be a pixel if the digital input image is two-dimensional. More generally, a voxel may be a n dimensional data structure if the input image is n dimensional. The n-dimensionality may result from e.g. a spatial—three-dimensional—image and/or a two-dimensional image having more than one color channel. For example, the input image may comprise at each voxel a plurality of intensity values at different spectral bands, such as any one or combination of an R, G, B value and/or other colors in the visible and non-visible-light range, UV, IR, NIR values, or a single grey scale intensity value.

Here and in the following, an input voxel marks a location $x_i$ in the input image, where $x_i$ may be represented by the n-tuple $x_i = \{x_1, \ldots, x_n\}$ of n local coordinates for a n dimensional image. For example, in a two-dimensional RGB image, n=5 holds, because there are two spatial coordinates x, y and three color channels of the image, R, G, B: $x_i = \{x_1, \ldots, x_5\} = \{x, y, R, G, B\}$. Alternatively, an RGB input image may be considered as three independent two-dimensional grey scale images $R(x, y)$, $G(x, y)$, $B(x, y)$, where R, G, B denote e.g. the light intensity I in the respective color band. The input image may also be three-dimensional. For a three-dimensional grey scale image, n=3, $x_i = \{x_1, x_2, x_3\} = \{x, y, z\}$.

For the deconvolution of a noisy input image, knowledge about the signal-to-noise ratio is needed. In practice, the image noise and the signal-to-noise ratio must be estimated. Thus, the deconvolution allows only computing an approximation $f(x_i)$ of the true input image $\hat{f}(x_i)$.

SUMMARY

In an embodiment, the present invention provides a method for a deconvolution of a digital input image ($I(x_i)$) having a plurality of input voxels ($x_i$), in particular a digital input image obtained from a medical observation device, such as a microscope or endoscope and/or using fluorescence. A local signal-to-noise ratio ($SNR(x_i)$) within an input region ($R(x_i)$) of the digital input image is computed. The input region consists of a subset of the plurality of input voxels of the digital input image and surrounding the current input voxel. A noise component ($\beta(SNR)$) is computed from the local signal-to-noise ratio, the noise component representing image noise ($n\,([h*f](x_i), n(x_i))$) in the deconvolution. The noise component is limited to a predetermined minimum noise value ($\beta_{min}$) for a local signal-to-noise ratio above a predetermined upper SNR threshold value ($SNR_{max}$) and is limited to a predetermined maximum noise value ($\beta_{max}$) for a local signal-to-noise ratio below a predetermined lower SNR threshold value ($SNR_{min}$).

BRIEF DESCRIPTION OF THE DRAWINGS

Embodiments of the present invention will be described in even greater detail below based on the exemplary figures. The present invention is not limited to the exemplary embodiments. All features described and/or illustrated herein can be used alone or combined in different combinations in embodiments of the present invention. The features and advantages of various embodiments of the present invention will become apparent by reading the following detailed description with reference to the attached drawings which illustrate the following.

DETAILED DESCRIPTION

Figure 1:
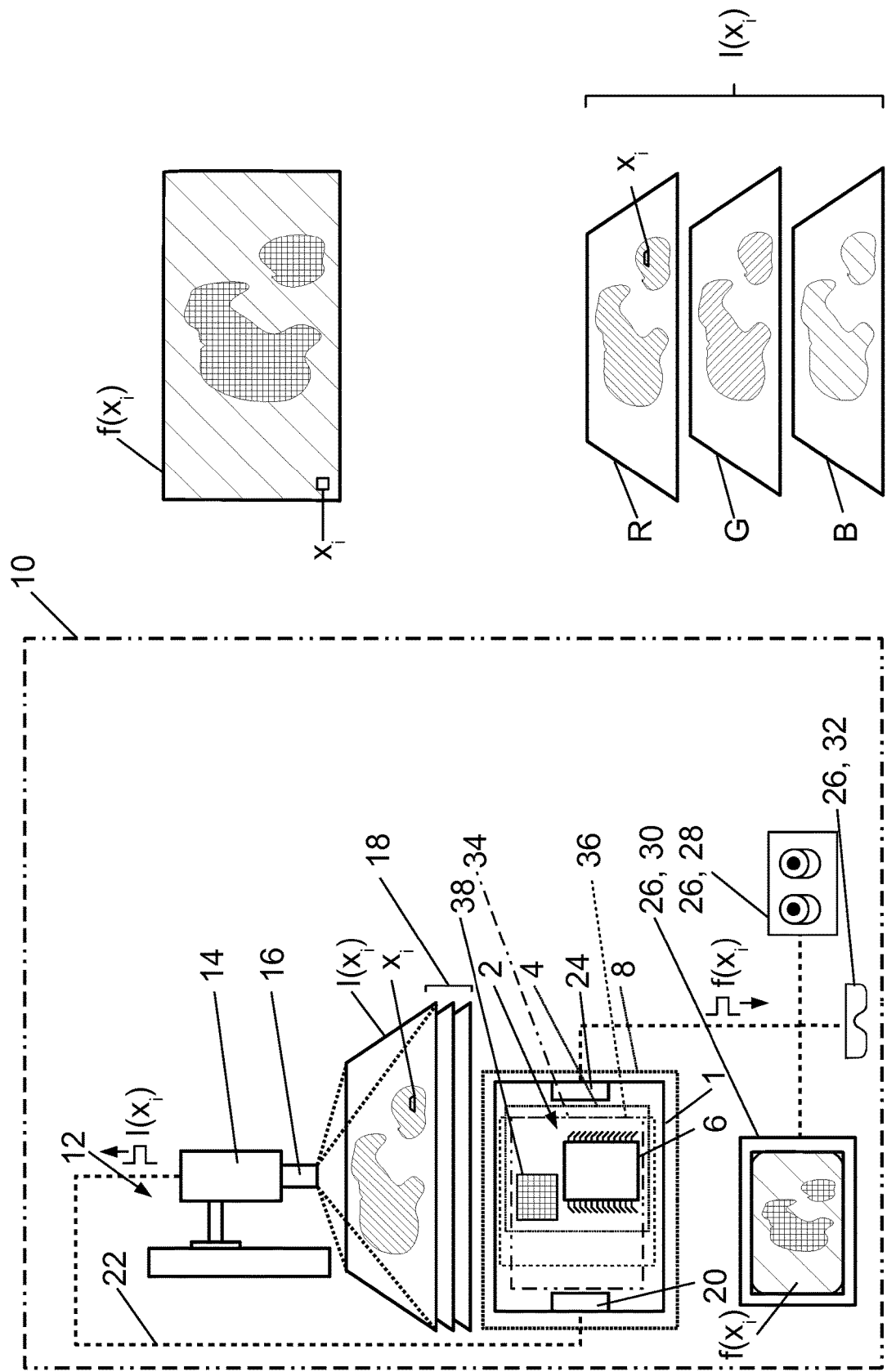
FIG. 1 shows a schematic representation of a medical observation apparatus according to an embodiment of the invention.

Standard deconvolution algorithms fail to deliver optimum results in specific applications, such as microscopy or endoscopy, in which the image characteristics in particular of fluorescence images differ from those encountered in other applications such as portrait, landscape, entertainment or artistic imagery. Moreover, an elaborated estimation and computation of the signal-to-noise ratio may quickly become too burdensome, in particular in view of the increased spatial resolution of modern images, to be performed in real time, especially if deconvolution has to keep up with a high frame rate, such as 60 Hz.

Embodiments of the present invention provide an apparatus and method with an improved deconvolution performance in particular in case of fluorescence, endoscope and/or microscope images. Further, embodiments of the present invention provide an apparatus and method, which are able to deconvolve a high-resolution digital input image in real time.

According to an embodiment of the invention the improved deconvolution is provided by a method, being related to a method for a deconvolution of a digital input image having a plurality of input voxels, in particular a digital input image obtained from a microscope or endoscope and/or using fluorescence, the method comprising the steps of:

computing a local signal-to-noise ratio within an input region of the digital input image, the input region consisting of a subset of the plurality of input voxels of the digital input image and surrounding the current input voxel;

computing a noise component from the local signal-to-noise ratio, the noise component representing image noise in the deconvolution;

wherein the noise component is limited to a predetermined minimum noise value for a local signal-to-noise ratio above a predetermined upper SNR threshold value and is limited to a predetermined maximum noise value for a local signal-to-noise ratio below a predetermined lower SNR threshold value.

Further, the improved deconvolution is provided according to an embodiment of the invention by an image processor for a medical observation apparatus, the image processor comprising:

a storage or memory section for storing a digital input image comprising a plurality of input voxels and a deconvolution engine for computing a deconvolved output image from the plurality of input voxels;

wherein the deconvolution engine comprises a noise component, which depends on a local signal-to-noise ratio at an input voxel, the local signal-to-noise ratio being computed in an input region consisting of a subset of the plurality of input voxels of the digital input image;

wherein the image processor contains a predetermined upper SNR threshold value and a predetermined lower SNR threshold value; and wherein the noise component is limited to a predetermined minimum noise value for a local signal-to-noise ratio above the predetermined upper SNR threshold value and to a predetermined maximum value for a local signal-to-noise ratio below the predetermined lower signal-to-noise threshold value.

The solution according to embodiments of the invention results in an improved quality i.e. reduced noise and increased sharpness, of the deconvolved output image by using a local signal-to-noise ratio, which is computed for the input region only. At the same time, the inventive method and apparatus according to embodiments realize a computational advantage by limiting the computation of the additive-noise component to the local input region surrounding the input voxel and by introducing upper and lower SNR threshold values.

One reason of the improved quality of the output images obtained by the inventive method and apparatus according to embodiments may be that particularly in images of biological matter, such as obtained by microscopes and endoscopes and/or by using fluorescence, the characteristics of the noise may differ across the entire digital input image. For example, the noise characteristics in a region of the image, which is in focus and shows an illuminated or fluorescing part of a cell or of tissue may not be the same as for a region containing mostly black or white background.

Moreover, it has been observed that for a large local signal-to-noise ratio above the predetermined upper SNR threshold, the image is good enough, and no further computation of the regularization parameter needs to be performed. Thus, for a signal-to-noise ratio above the predetermined upper SNR threshold, the noise component can be set to a predetermined minimum noise value.

Further, it has been observed that for very a small local signal-to-noise ratio, SNR<1 or even SNR<<1, allowing the noise component to increase beyond a predetermined maximum value does not lead to better results in the deconvolved output image. Thus, the noise component is limited to the predetermined maximum SNR value if the signal-to-noise falls below a predetermined lower SNR threshold.

The solution according to embodiments of the invention may be further improved by adding one or more of the following features, which can be combined independently from one another.

For example, the image processor may be a software device, a hardware device, or a combination of both a hardware device and a software device. The image processor may comprise at least one of a CPU, an array processor, a GPU, an ASIC, a FPGA and/or a FPU. The image processor may in particular be adapted to perform array and/or parallel processing assembly. The image processor may comprise one or more software modules that, in operation, alter the physical structure of a processor by e.g. altering transistor states.

The signal-to-noise ratio $SNR(x_i)$ at a voxel $x_i$ of the input image may be computed in the input region $R(x_i)$ as the ratio of signal level or strength $S(x_i)$ to noise level $N(x_i)$:

$$SNR(x_i) = \frac{S(x_i)}{N(x_i)}.$$

In another embodiment, the signal-to-noise ratio may be computed as:

$$SNR(x_i) = 10 \log_{10} \frac{S(x_i)}{N(x_i)}.$$

Once the local signal-to-noise ratio has been computed for all input voxels $x_i$ of the digital input image, the resulting n-dimensional array $SNR(x_i)$ may be blurred using a linear filter such as a low-pass or a Gaussian filter to ensure smooth transitions between the voxels.

Preferably, only the pixels in a predetermined input region surrounding the current voxel are used to compute the local signal-to-noise ratio at that particular current voxel. In particular, the noise level $N(x_i)$ and the signal level $S(x_i)$ may each be computed in the (same) input region only.

According to one embodiment, the signal level or strength $S(x_i)$ at an input voxel $x_i$ may be estimated by convolving the input image $I(x_i)$ with a blur kernel $k_b(x_i)$ in the input region $R(x_i)$ for the local SNR estimation and taking the maximum value of this convolution:

$$S(x_i) = \max_{\Omega R(x_i)} [[I * k_b](x_i)],$$

where $\Omega$ is the region where the convolution is carried out.

According to one embodiment, the input region may contain between 200 and 1000 input voxels, more preferably between 300 and 700 input voxels and most preferably around 500 input voxels. An input region of this size is sufficiently large to give reliable statistical estimates and at the same time is not too large to extend to regions in an image, which have a different noise characteristics.

The blur kernel may be a linear filter, such as a Gaussian filter, e.g. having the following form:

$$k_b(x_i) = \frac{1}{(2\pi)^{n/2}\prod_{i=1}^{n}\sigma_i} e^{-\sum_{i=1}^{n}\frac{1}{2}\left(\frac{x_i}{\sigma_i}\right)^2},$$

wherein $0.5 < \sigma_i < 1.0$, in particular $\sigma_i \approx 0.75$. The linear filter may have e.g. a dimension of 3×3 or 5×5. On a GPU, directly computing such a two-dimensional blur kernel is faster than separate one-dimensional passes using e.g. a 1×3 or 1×5 kernel.

According to another embodiment, the noise level $N(x_i)$ at an input voxel $x_i$ may be estimated in an advantageous embodiment by computing a variance based on the digital input image in the input region as follows:

$$N(x_i) = \sqrt{\text{var}[I'(x_i)]},$$

Herein, $I'(x_i)$ is a derivative value or gradient of the input image at location $x_i$ in any of the n dimensions of the input image and of any order. The derivative value $I'$ may for example be obtained by applying a linear discrete operator $\mathbb{D}$ to the input image I in the input region R:

$$I'(x_i) = \mathbb{D} I(x_i).$$

In particular, $\mathbb{D}$ may be an edge detection filter, such as a Sobel or Laplace operator, or a first, second or higher order gradient operator such as $$\frac{\partial}{\partial x}, \frac{\partial}{\partial y}, \frac{\partial^2}{\partial x \partial y}, \frac{\partial^2}{\partial y^2}, \text{ or } \frac{\partial^2}{\partial x^2},$$

or any linear combination of such linear operators. For example, the application of the second-order gradient operator $$\mathbb{D} \triangleq \frac{\partial^2}{\partial x \partial y}$$

in the discrete may be represented in the two-dimensional case as:

$$\mathbb{D} I_{ab} = I_{(a+1)(b+1)} - I_{(a+1)b} - I_{a(b+1)} + I_{ab}$$

at the input voxel $x_i = \{a, b\}$, $\Omega \in R(x_i)$, and $I_{ab} = I(a, b)$, where $\Omega$ is the considered volume or region.

In one embodiment, the variance may be computed as:

$$\text{var}[I'(x_i)] = \mathbb{E}\left[(I'(x_i) - \mathbb{E}[I'(x_i)])^2\right],$$

where $\mathbb{E}$ is a norm of an n-dimensional array, such as a mean or expected value operator, for example $$\mathbb{E}(z) = \frac{1}{Q}\sum_{q=1}^{Q} z_q$$

in the one-dimensional case, where $z_q$ is a one-dimensional discrete array. As is explained further below, this form is particularly suited for computing the noise level in a computationally highly efficient manner using a summed-area table.

For computing the (local) signal-to-noise ratio $SNR(x_i)$, and for blurring the signal-to-noise ratio, the image processor may comprise a signal-to-noise computation engine, which may be a hardware or a software component, or a combination of both, of the image processor. The signal-to-noise computation engine may comprise in one embodiment a separate hardware component, such as at least one CPU, GPU, FPU and/or designated IC, e.g. an ASIC, or any combination thereof, and/or a separate software module, such as one or more subroutines. The signal-to-noise computation engine may in particular be configured to compute also at least one of the signal level and the noise level.

As stated above, at least one of the signal level and the noise level at an input voxel $x_i$, preferably both, may be computed in the input region $R(x_i)$ only. The input region thereby consists of only a subset of the input voxels of the digital input image.

The input region preferably is a contiguous region of input voxels. The input region preferably surrounds the current input pixel or voxel, for which the signal-to-noise ratio $SNR(x_i)$ is computed. Thus, the signal-to-noise ratio is a local value, which varies from input voxel to input voxel, as different input regions, each of preferably the same shape and size, are used for each input voxel.

Preferably, the input region, in which the input voxels are considered for computation of the signal and/or noise level, has at least two-fold symmetry. The input region may deviate from an n-dimensional cuboid shape by a plurality of smaller n-dimensional cuboid regions, each of which is contiguous. For example, the input region may differ in the two-dimensional case from a rectangle or a square shape by one or more rectangles that themselves are not part of the input region.

In particular, the input region may be a n-dimensional Gaussian, circular, Mexican hat or star-shaped contiguous arrangement, or a discrete approximation thereof, of input voxels, in particular of rectangles comprising a plurality of input voxels.

The input region may have a shape that results from superimposing a plurality of n-dimensional cuboid regions of input pixels. In the two-dimensional case, the input region may be constituted by a superposition of rectangles, which each may comprise at least 2×2 or 4×4 voxels.

According to one embodiment, a larger weight may be assigned to input voxels in the input region that are closer to the current input voxel at which the noise level is computed than to input voxels in the input region that are spaced further apart from the current input voxel. Such a weighting leads to a smooth fading out of the input region towards its borders and thus to a smoother distribution of the local noise levels across the input voxels.

The computation of the local noise level using $\mathbb{E}[(I'(x_i) - \mathbb{E}[I'(x_i)])^2]$ within the input region is preferably done using a summed-area table. This allows determining the local signal-to-noise ratio in a computationally highly efficient manner. A description of summed-area tables is found in Crow, Franklin C.: "Summed-area tables for texture mapping", ACM SIGGRAPH computer graphics, (18) 3, 1984. An n-dimensional version of a summed-area table is described in Tapia, Ernesto: "A note on the computation of high-dimensional integral images", Pattern Recognition Letters, 32 (2), 2011.

For each parameter that needs to be summed up over the input region, a separate summed-area table may be generated, preferably before the noise level is computed.

For example, when computing the variance as $\mathbb{E}[(I'(x_i) - \mathbb{E}[I'(x_i)])^2]$, a summed-area table may be generated for $\mathbb{E}[I'_i(x_i)]$ and, once this summed-area table has been computed, a separate summed-area table may be generated for $\mathbb{E}[(I'(x_i) - \mathbb{E}[I'(x_i)])^2]$.

The at least one summed-area table may be part of the image processor, e.g. by being stored at least temporarily in a storage section of the image processor and/or by an instruction allocating memory of the image processor for storing a summed-area table.

Defining the noise level in terms of a variance, which in turn is computed using a summed-area table, leads to a computationally highly efficient deconvolution algorithm, which decreases considerably the additional burden that the computation of a plurality of local signal-to-noise ratios instead of a single global signal-to-noise ratio creates.

Each of the summed-area tables is a digital array of values having the same dimensionality as the input image.

Whereas it is described above that the noise level may be estimated by computing the variance, i.e. the second statistical moment, of the derivative value in the input region, it is also possible to use a higher, $n^{th}$, statistical moment for computing the noise level. In general, $n^{th}$ the statistical moment:

$$N(x_i) = \mathbb{E}[(I'(x_i) - \mathbb{E}[I'(x_i)])^n]$$

may also be computed using summed-area tables.

Using summed-area tables, the size and shape of the input region may be implicitly defined by the selection of coordinates within the summed-area table relative to the current input voxel, which coordinates define the blocks, i.e. n-dimensional cuboids, of summed values that are used for computing the statistical moment. By combining the blocks of the summed-area tables to construe the input region, input voxels located where the blocks overlap automatically obtain a larger weight. It is in such a case preferred that the overlap of the blocks is located at the center of the input region. Thus, this region may automatically be assigned a larger weight.

In case of the image processor according to the invention, the image processor may comprise a summed-area-table generator, the summed-area-table generator being configured to compute a summed-area table of the region and to compute the noise level using the summed-area table. The summed-area table generator may be a hardware device, a software device, or a combination of both a hardware and a software device.

To further increase computational efficiency, at least one summed-area table of the input region may be generated by a parallel computation of prefix sums. In order to perform this step quickly, the image processor, or in particular the summed-area table generator preferably comprises at least one prefix-sum generator, which may be a hardware device, a software device or a combination of the two. The hardware device may comprise an array processor, such as a GPU, or a parallel-processing assembly comprising e.g. a plurality of GPUs, CPUs and/or FPUs. The software device may comprise an instruction set for the hardware device. In operation, the hardware set may change its structure due to the instruction set of the software device to carry out the parallel computation of the prefix sums. The prefix-sum generator is configured to compute a prefix sum in a parallel manner.

The deconvolution may be done using different methods.

For example, a Wiener deconvolution may be carried out using a Wiener filter. In this embodiment, the output image $f(x_i)$ can be estimated from the observed image, i.e. the digital input image as follows:

$$f(x_i) = \mathcal{F}^{-1}\left[\frac{\mathcal{F}[h(x_i)]^* \mathcal{F}[I(x_i)]}{|\mathcal{F}[h(x_i)]|^2 + \beta}\right],$$

where $\mathcal{F}$ denotes the n-dimensional discrete Fourier transform of the quantity in brackets and $\mathcal{F}[h(x_i)]^*$ is the complex conjugate of the discrete Fourier transform of $h(x_i)$. The term:

$$\mathcal{W} = \frac{F[h(x_i)]^*}{|F[h(x_i)]|^2 + \beta}$$

is the Wiener filter. The term $\beta$ is the noise component of the Wiener filter, which in one preferred embodiment is chosen to depend on the local signal-to-noise ratio SNR as described above: $\beta = \beta(SNR(x_i))$.

In another embodiment, a maximum a posteriori deconvolution, such as a Lucy-Richardson deconvolution, may be used. The Lucy-Richardson deconvolution is e.g. described in Fish D. A.; Brinicombe A. M.; Pike E. R.; Walker J. G.: "Blind deconvolution by means of the Richardson-Lucy algorithm", Journal of the Optical Society of America A, 12 (1), p. 58-65 (1995). The Lucy-Richardson deconvolution may in particular use scaled-gradient projection for increased computation performance.

In the Lucy-Richardson deconvolution, the following iterative computation of the output image is performed:

$$f^{(k+1)}(x_i) = \frac{f^{(k)}(x_i)}{1 + \beta V(x_i)} h^T(x_i) * \left(\frac{I(x_i)}{[h * f^{(k)}](x_i) + b(x_i)}\right),$$

with $f^{(k)}(x_i)$ as the output image, i.e. the estimate of the true image, in the k-th iteration. Convolution is denoted with $*$ and $h^T(x_i) = h(-x_i)$ is the flipped PSF (point spread function) of the imaging system or the lens. The function $V(x_i)$ is the derivative of the regularization function, $R_{reg}(x_i)$:

$$V(x_i) = \frac{\delta R_{reg}}{\delta f^{(k)}(x_i)}.$$

The regularization function $R_{reg}(x_i)$ may be at least one of the total variation $\|\nabla f(x_i)\|^2$, i.e. the norm of the gradient, a Tikhonov regularization $\|f(x_i)\|^2$ and Good's roughness $$\left\|\frac{\nabla f(x_i)}{f(x_i)}\right\|^2,$$

or any preferably linear combination of such functions.

The term $b(x_i)$ is a background parameter. Preferably, the background parameter is chosen to be dependent on the local signal-to-noise ratio: $b(x_i) := b(SNR(x_i))$. According to a further embodiment, the background parameter may be a linear function of the local signal-to-noise-ratio.

In an embodiment that leads to a particularly sharp deconvolved image, the background parameter attains a minimum value if the local signal-to-noise ratio is above the predetermined lower SNR threshold value. Additionally or alternatively, the background parameter may attain a maximum value if the local signal-to-noise ratio is below the predetermined upper SNR threshold value.

The background parameter may include a scaling factor that depends on the noise level as e.g. computed above for the entire input image.

The parameter β corresponds to the noise component of the deconvolution and is chosen in one embodiment of the invention to depend on the local signal-to-noise ratio. β:=β(SNR($x_i$)). The local signal-to-noise-ratio may be computed as described above.

Irrespective of the particular deconvolution method applied to the digital input image, the noise component β(SNR) is computed as a continuous function of the local signal-to-noise ratio. In particular, the noise component may be a monotonical, preferably strictly monotonical function decreasing between a predetermined maximum noise value, $β_{max}$, at the predetermined lower SNR threshold value, $SNR_{min}$, β($SNR_{min}$)=$β_{max}$ and a predetermined minimum noise value, $β_{min}$, at a predetermined maximum SNR value, $SNR_{max}$.

In particular, the noise component β may comprise at least one of a linear function, a polynomial function and a trigonometric function depending on $$\frac{1}{SNR}.$$

According to one specific embodiment, which leads to good deconvolution results, $β_{max}$ may be chosen to be between 1 and 10% of the dynamic range, in particular about 5%. In the latter case, $β_{max}$ may be about 0.05. The value for $SNR_{min}$ may be zero, i.e. $SNR_{min}$=0.

In particular for digital input images recorded by a microscope or an endoscope, the predetermined maximum SNR value, $SNR_{max}$, at which the regularization parameter is truncated, is larger than 2, preferably smaller than 5 and most preferred about 3.

Good results for deconvolution have been obtained if the gradient of the noise component, $$\frac{dβ(SNR)}{dSNR},$$

is smaller at SNR=0 and/or at the predetermined maximum SNR value $SNR_{max}$ than in the middle region between those two values, i.e. at about $$\frac{SNR_{max} - SNR_{min}}{2}.$$

According to a further preferred embodiment, which leads to very good deconvolution results, the noise component β is computed using:

$$β(SNR(x_i)) = \max\left[SNR_{min'}, \frac{β_{max}}{2'}\left\{1 - \arctan\left(\frac{\left(2\frac{SNR(x_i)}{SNR_{max}} - 1\right)π}{2}\right)\right\}\right],$$

where $SNR_{max}$ is the predetermined maximum SNR value

The improved deconvolution is also provided by a medical observation device, such as a microscope or an endoscope, comprising an image processor in at least one of the above embodiments.

Finally, another embodiment of the invention also relates to a non-transitory computer readable medium storing a program causing a computer to execute the image processing method in any one of the above-mentioned embodiments.

In the following, a practical implementation of the invention is described with reference to the drawings using one or more embodiments. The description serves as an example only and in no way restricts the invention and its features to what is shown in the drawings and explained below. Rather, the combination of features shown in the embodiments may be altered as described above. For example, one or more of the features of an embodiment can be omitted if its or their technical effect is not needed for a particular implementation. Likewise, one or more of the above-described features may be added if the technical effect of that particular feature or features is advantageous for a particular application.

In the drawings, the same reference numerals are used for elements that correspond to each other with respect to at least one of structure and function.

First, the structure of an image processor 1 according to an embodiment of the invention is described with reference to FIG. 1. The image processor 1 may comprise one or more hardware components 2, such as a memory 4 and an integrated circuit 6. The integrated circuit 6 may comprise at least one CPU, GPU, FPU, ASIC FPGA and/or any combination thereof. The image processor 1 may be part of a computer 8, such as a personal computer, laptop or tablet. Instead of, or in addition to the one or more hardware components 2, the image processor 1 may comprise software, which is configured to run on the one or more hardware components 2.

As shown exemplarily in FIG. 1, the image processor 1 may be part of a medical observation device 10, such as a microscope 12, in particular a confocal scanning microscope, or an endoscope.

Using an optical recording device, such as a camera 14 having a lens 16, the medical observation device 10 records a digital input image I($x_i$) which comprises input voxels $x_i$. The digital input image I($x_i$) is represented by a n-dimensional array of digital values, which represent e.g. intensity in a color channel or, equivalently, a spectral band. For example, a digital input image I($x_i$) may consist of one or more color channels R, G, B in the case of an RGB camera.

The camera 14 may be a RGB-camera, a monochrome camera, a multispectral or a hyperspectral camera or an assembly comprising a combination of such cameras, of which the images may be combined. The camera 14 may be in particular a camera, which is sensitive to the spectral band or spectral bands, in which a fluorophore emits fluorescence.

The digital input image I($x_i$) may be two- or more dimensional, wherein both spatial and color dimensions may be considered in the dimensionality. Although the camera 14 may record a time-series 18 of digital input images I($x_i$), a single digital input image I($x_i$) is considered in the following. This single digital input image may nonetheless have been computed from more than one original input images, as is e.g. the case with images obtained by z-stacking or with HDR-images. The digital input image $I(x_i)$ may also be a stereoscopic image.

In the case of an endoscope, a lens 16 of the microscope 12 may be replaced by fiber optics. Otherwise, the endoscope and the microscope may be considered as being identical for the purpose of the invention.

The image processor 1 may comprise several components, of which each may be configured as a hardware device, as a software device, or as a combination of both a hardware and a software device, like the image processor 1 itself.

For example, the image processor 1 may comprise an input interface 20 for inputting the digital input image $I(x_i)$. The input interface 20 may provide a wired or wireless connection 22 to the camera 14. The digital input image $I(x_i)$ is sent via the connection 22 from the camera 14 to the image processor 1. The input interface 20 may provide one or more standard connections for receiving the digital input image, such as a HDMI, DVI, Bluetooth, TCP/IP, or RGB connection as well as any other type of connection suited for the task of transmitting video and/or image data.

The image processor 1 may further comprise an output interface 24 for outputting a deconvolved digital output image $f(x_i)$ to a storage medium and/or one or more display devices 26, such as an eyepiece 28, a monitor 30 and/or virtual-reality glasses 32. Any of the one or more display devices 26 may be stereoscopic or holographic.

The one or more display devices 26 may be connected wired and/or wireless to the output interface 24. The output interface 24 may employ one or more data transmission standards for sending the deconvolved digital output image $f(x_i)$ to the one or more digital display devices, such as HDMI, DVI, Bluetooth, TCP/IP, or RGB, or any other standard that allows sending digital image data.

The image processor 1 is configured to perform a deconvolution of the digital input image $I(x_i)$ to compute the deconvolved digital output image $f(x_i)$.

In the embodiment shown, the image processor 1 comprises a deconvolution engine 34, which is configured to perform the deconvolution of the digital input image $I(x_i)$. The deconvolution may be a Wiener deconvolution or a maximum a posteriori deconvolution, in particular a Lucy-Richardson deconvolution.

The image processor 1 may further comprise a summed-area-table generator 36, which is configured to compute at least one summed-area table 38 of the digital input image $I(x_i)$ using a parallel prefix sum algorithm. The summed-area-table generator 36 may, as the image processor 1, be a hardware device, a software device, or a combination of both.

In the embodiment shown, the summed-area table generator 36 is configured to compute a summed-area table of both $\mathbb{E}[\mathbb{D} I(x_i)]$ and of $\mathbb{E}[(\mathbb{D} I(x_i) - \mathbb{E}[\mathbb{D} I(x_i)])^n]$ for the entire input image. Here, $\mathbb{D}$ is a linear derivative operator, such as a Sobel or a Laplace filter or a gradient of any order. In the embodiment shown, $$\mathbb{D} \triangleq \frac{\partial^2}{\partial x \partial y}$$

and n=2, $\mathbb{E}$ denotes the mean of an array.

From the summed-area tables, a background parameter $b_0$ of the overall image can be computed quickly as follows:

$$b_0(x_i) = 0.2 \sqrt[t]{\mathbb{E}_\Omega[(\mathbb{D} I(x_i) - \mathbb{E}_\Omega[\mathbb{D} I(x_i)])^2]} \forall (x_i \in I(x_i)).$$

The expression $\mathbb{E}_\Omega$ is used to denote that the operation is carried out only in the region $\Omega$ which is equal to or a subset of the input region $R(x_i)$. For computing the local signal-to-noise ratio at a voxel $x_i$ of the input image, an input region $R(x_i)$ is defined. The input region surrounds the voxel $x_i$ at which the signal-to-noise ratio $SNR(x_i)$ is to be computed at a later step. The input region is composed of rectangular blocks in case of a two-dimensional input image and of cuboids in case of a n-dimensional input image. The input region $R(x_i)$ contains between 300 and 700 voxels, preferably about 500 voxels.

In the exemplary embodiment, the input image is two-dimensional and the input region is constituted of rectangles. Preferably, a plurality of rectangles overlap at the center of the input region $R(x_i)$, in particular at the current input voxel $x_i$. Such an overlap leads automatically to a larger weight of the center region when a summed-area table is used. The increased weight at the center of the input region creates a smooth tapering out at the edges of the input region and thus to better results.

Figure 2:
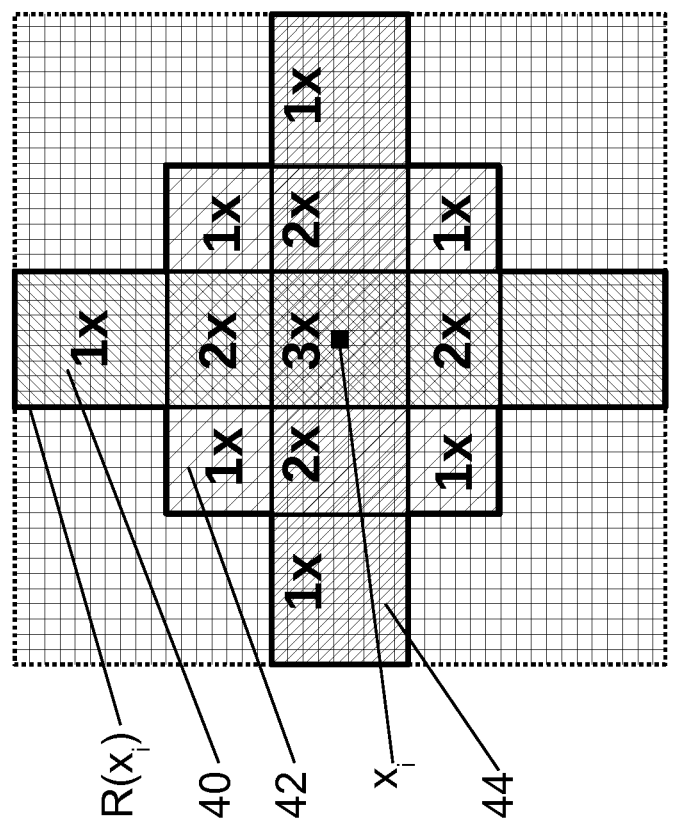
FIG. 2 shows an example of an input region.

An example of an input region $R(x_i)$ centered on the current voxel $x_i$ resulting from the superposition of three rectangles 40, 42, 44 is shown in FIG. 2. The input region may have at least two-fold symmetry. Of course, other shapes of input regions may also be used. It is preferred that the input region $R(x_i)$ approximates a circular region. For increased computational efficiency in using the summed-area table, the input region should contain as few rectangles and/or as large rectangles as possible. By construing the input region from a superposition of rectangles, a weighing takes place automatically. In FIG. 2, the weighing factors are indicated in the different rectangular parts of the input region. Parts closer to the center of the input region, where the current voxel is located have a higher weight than parts farther away from the center. In the example shown, the weighing factors are 3, 2 and 1, respectively.

The noise level $N(x_i)$ at an input voxel $x_i$ is then computed by using only the voxels in the input region $R(x_i)$. The shape of the input region $R(x_i)$ is determined implicitly by defining the rectangles 40, 42, 44 of which the sum is extracted from the summed-area tables. The noise level is computed as follows:

$$N(x_i) = 0.2 \sqrt[t]{\mathbb{E}_\Omega[(\mathbb{D} I(x_i) - \mathbb{E}_\Omega[\mathbb{D} I(x_i)])^2]} \forall (x_i \in R(x_i)).$$

Next, the signal level $S(x_i)$ is computed by again using only the voxels in the input region $R(x_i)$ as follows:

$$S(x_i) = \max_{\Omega = R(x_i)} [[I * k_b](x_i)].$$

The expression $k_b(x_i)$ denotes a two-dimensional Gaussian blur kernel:

$$k_b(x_i) = \frac{8}{9\pi} e^{-\frac{8}{9} \sum_{i=1}^{1} x_i^2}.$$

Of course, other blur kernels may also be used.

Once both the noise level $N(x_i)$ and the signal level $S(x_i)$ have been determined for each of the input voxels $x_i$, the signal-to-noise ratio is determined for each input voxel $x_i$ as:

$$SNR(x_i) = \frac{s(x_i)}{N(x_i)}.$$

The resulting digital array $SNR(x_i)$ has the same dimensionality as the input image $I(x_i)$. Preferably, the array $SNR(x_i)$ is low-pass filtered or, more preferably, blurred with a 3×3 or a 5×5 Gaussian filter with σ=0.8.

If it is chosen to use e.g. a Lucy-Richardson deconvolution, the following iteration is carried out to compute the deconvolved output image $f(x_i)$:

$$f^{(k+1)}(x_i) = \frac{f^{(k)}(x_i)}{1+\beta(SNR(x_i))V(x_i)}h^T(x_i) * \left(\frac{J(x_i)}{[h*f^{(k)}](x_i)+b(x_i)}\right),$$

until the following convergence criterion has been met:

$$\frac{\sum_{\text{over all elements}} |f^{(k)}(x_i) - f^{(k-1)}(x_i)|}{\sum_{\text{over all elements}} (f^{(k)}(x_i) + f^{(k-1)}(x_i))} < 2 \times 10^{-5}$$

Here, $f^{(k)}(x_i)$ represents the deconvolved output image at the $k^{th}$ iteration. The noise component $\beta(SNR(x_i))$ is computed as $$\beta(SNR(x_i)) = \max\left[SNR_{min'}, \frac{\beta_{max}}{2'}\left\{1-\arctan\left(\frac{\left(2\frac{SNR(x_i)}{SNR_{max}}-1\right)\pi}{2}\right)\right\}\right],$$

wherein $SNR_{max}$ represents a maximum SNR threshold value, which is set to 4 in the current embodiment.

The background parameter $b(x_i)$ is chosen to be a linear function of the signal-to-noise ratio in the current embodiment. It is computed as $$b(x_i) = \max\left[0, b_0\left(1 - \frac{SNR(x_i)}{SNR_{max}}\right)\right].$$

Finally, the expression $V(x_i)$ is computed as $$V(x_i) = \frac{\delta}{\delta f(x_i)}\left\|\frac{\nabla f(x_i)}{f(x_i)}\right\|^2 = -2\nabla\left(\frac{\nabla f(x_i)}{f(x_i)}\right)$$

If the convergence criterion has been met, $f^{(k+1)}(x_i)$ represents the digital deconvolved output image. The output image $f^{(k+1)}(x_i)$ is a digital array of values and has the same dimensionality as the input image $I(x_i)$.

The output image $f^{(k+1)}(x_i)$ is then output to the output interface 24 from where it may be passed on to any of the one or more display devices 26 for display and/or a storage device.

Figure 3:
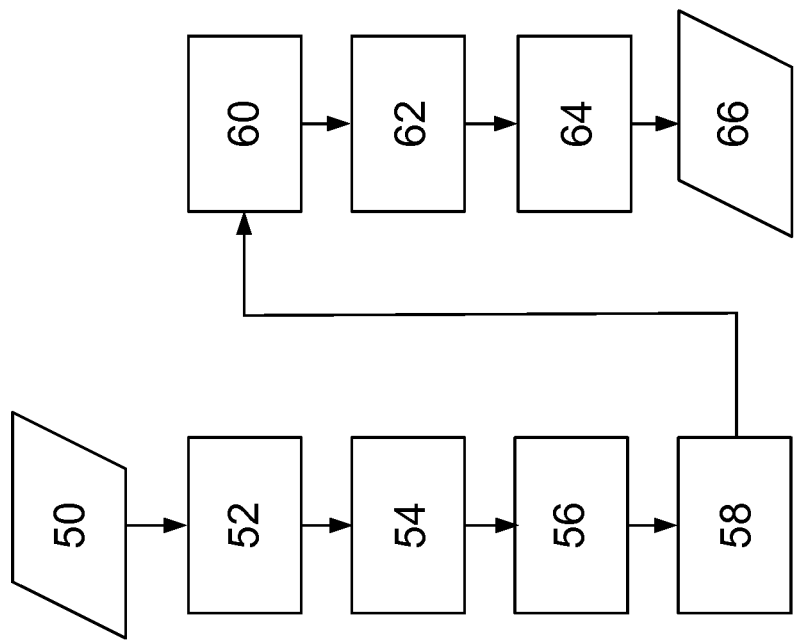
FIG. 3 shows a schematic flowchart of a method according to an embodiment of the invention.

The deconvolution carried out by the image processor 1 may be summarized as shown in FIG. 3.

At the start of the method, constants and functions used in the deconvolution may be selected by a user, or automatically, e.g. as preset values, by the image processor 1.

For example, the upper SNR threshold value, $SNR_{max}$, the lower SNR threshold value, $SNR_{min}$, may be defined or altered.

The form of the noise component $\beta(SNR(x_i))$ may be selected by a user e.g. from a list of available functions.

The specific form of the operators $\mathbb{D}$ and/or $\mathbb{E}$ and/or the order of the statistical moments for computing the noise level may be selected by a user.

The preferably linear filter used for blurring the array $SNR(x_i)$ and/or the blur kernel $k_b(x_i)$ may be selected by a user e.g. from a list of available filters.

The particular deconvolution method may be selected by a user. For example, the user may select between a Wiener deconvolution and a maximum a posteriori deconvolution such as a Lucy-Richardson deconvolution.

If a Wiener deconvolution is selected, the user may specify or select a transfer function, e.g. from a library, such as a point-spread function appropriate for the current recording system. Alternatively, the transfer or point-spread function may be stored in a memory or storage section and be automatically determined from the set-up of the microscope or endoscope, e.g. by automatically detecting the type of lens which is currently in use.

If a Lucy-Richardson deconvolution is used, the regularization function $R_{reg}(x_i)$ may be selected by a user e.g. from a list of available functions, such as the total variation $\|\nabla f(x_i)\|^2$, i.e. the norm of the gradient, a Typhonov regularization $\|f(x_i)\|^2$ and Good's roughness $$\left\|\frac{\nabla f(x_i)}{f(x_i)}\right\|^2$$

or any combination thereof. The function used in the background parameter $b(x_i)$ may be selected by a user, e.g. by selecting a function from a list.

A user may define the shape and size of the input region $R(x_i)$, e.g. by selecting from a list of available input regions or by specifying an individual input region.

Further, any constant used in the deconvolution may be set and/or altered by the user.

In a step 50, the digital input image $I(x_i)$ is acquired. This step may be carried out by the camera 14 or by the image processor 1, which may e.g. compute the digital input image $I(x_i)$ from one or more digital images residing in the memory 4, acquired from the camera 14, or a combination of both.

In the next step 52, the at least one summed-area table 38 is computed from the input image $I(x_i)$ preferably using a parallel algorithm such as a prefix sum. Step 52 may be carried out at any time before the deconvolution is computed. As indicated above, two summed-area tables 38 are computed if the noise level is computed using a statistical moment having an order of at least 2.

Once the summed-area tables 38 are available, the local noise level $N(x_i)$ is computed for every voxel $x_i$ in the input image $I(x_i)$ in step 54, using only the voxels in the input region $R(x_i)$ around the current voxel $x_i$.

At any time before computing the deconvolution, the local signal level $S(x_i)$ is determined for every input voxel $x_i$ of the input image $I(x_i)$ as described above, e.g. using a Gaussian blur kernel, and indicated at step 56. For the computation of the signal level $S(x_i)$ at any input voxel $x_i$ of the input image $I(x_i)$, only the voxels $x_i$ in the input region $R(x_i)$ are used.

Once the signal level $S(x_i)$ and the noise level $N(x_i)$ are available, the signal-to-noise ratio is determined for every input voxel $x_i$ of the input image at step 58.

The resulting array $SNR(x_i)$ containing the signal-to-noise ratio for each voxel $x_j$ may be blurred using a low-pass and/or a Gaussian filter. This is denoted by step 60.

At step 62, the deconvolution is carried out and the output image $f(x_i)$ is computed The output image $f(x_i)$ may undergo further post-processing as is indicated at step 64. For example, the output image may be assigned pseudo-colors and/or be merged with other images if the input image $I(x_i)$ is a fluorescence image in the emission band of a fluorescing fluorophore.

At step 66, the output image $f(x_i)$ may be displayed on a display device 26 and/or stored in a storage device, such as a disk or memory card.

Figure 6:
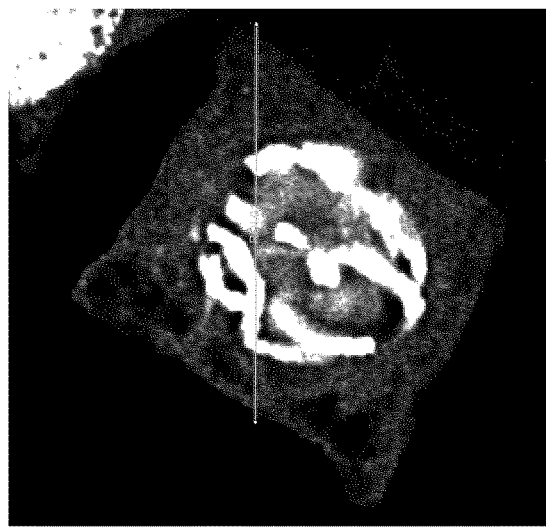
FIG. 6 shows an output image computed from the input image of FIG. 3 using the deconvolution according to an embodiment of the invention.
Figure 5:
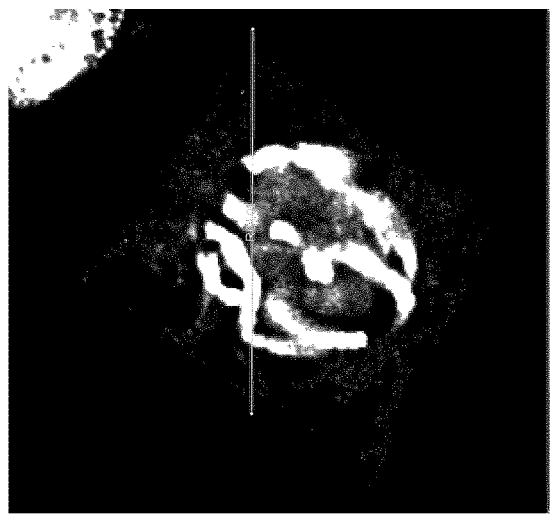
FIG. 5 shows an output image computed from the input image of FIG. 3 using a known deconvolution method.
Figure 4:
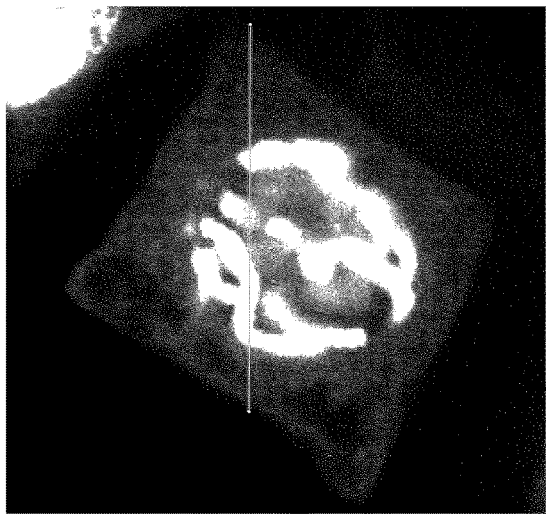
FIG. 4 shows an input image before deconvolution.

The results of a deconvolution of an input image $I(x_i)$ become apparent from FIG. 4 to 6. In FIG. 4, input image $I(x_i)$ is shown. In FIG. 5, an output image is shown as obtained by a conventional Lucy-Richardson deconvolution in which only the global signal-to-noise ratio for the entire image was used in the background parameter and the noise component.

In FIG. 6, the result of using the deconvolution as described in the context of the exemplary embodiment of the invention is shown.

A comparison of FIG. 5 and FIG. 6 clearly shows that the deconvolution of the embodiment according to the invention is capable of reducing noise more efficiently and of rendering finer detail than the conventional deconvolution.

At the same time, defining the noise level in terms of a statistical moment and of summed-area tables computed with prefix sums allows a quick computation of the deconvolved output image $f(x_i)$ although, in principle, the use of a local signal-to-noise ratio is computationally more tedious than using a global signal-to-noise ratio.

While embodiments of the invention have been illustrated and described in detail in the drawings and foregoing description, such illustration and description are to be considered illustrative or exemplary and not restrictive. It will be understood that changes and modifications may be made by those of ordinary skill within the scope of the following claims. In particular, the present invention covers further embodiments with any combination of features from different embodiments described above and below. Additionally, statements made herein characterizing the invention refer to an embodiment of the invention and not necessarily all embodiments.

The terms used in the claims should be construed to have the broadest reasonable interpretation consistent with the foregoing description. For example, the use of the article "a" or "the" in introducing an element should not be interpreted as being exclusive of a plurality of elements. Likewise, the recitation of "or" should be interpreted as being inclusive, such that the recitation of "A or B" is not exclusive of "A and B," unless it is clear from the context or the foregoing description that only one of A and B is intended. Further, the recitation of "at least one of A, B and C" should be interpreted as one or more of a group of elements consisting of A, B and C, and should not be interpreted as requiring at least one of each of the listed elements A, B and C, regardless of whether A, B and C are related as categories or otherwise. Moreover, the recitation of "A, B and/or C" or "at least one of A, B or C" should be interpreted as including any singular entity from the listed elements, e.g., A, any subset from the listed elements, e.g., A and B, or the entire list of elements A, B and C.

REFERENCE NUMERALS

1 image processor
2 hardware component
4 memory
6 integrated circuit
8 computer
10 medical observation device
12 microscope
14 camera
16 lens
18 time-series of input images
20 input interface
22 connection between camera and image processor
24 output interface
26 display device
28 eyepiece
30 monitor
32 virtual reality glasses
34 deconvolution engine
36 summed-area-table generator
38 summed-area table
40, 42, 44 rectangles constituting the input region
50 step of acquiring the digital input image
52 step of computing the summed-area table
54 step of computing the noise level
56 step of computing the signal level
58 step of computing the signal-to-noise ratio
60 step of blurring the signal-to-noise ratio array
62 step of computing the output image by deconvolving the input image
64 post-processing of the output image
66 step of displaying and/or storing the output image
$b_0$, $b(x_i)$ background parameter
$f(x_i)$ deconvolved digital output image
$f^{(k+1)}(x_i)$ $(k+1)^{th}$ iteration in an iterative computation of the output image
$\hat{f}(x_i)$ true image
$h(x_i)$ transfer function of recording system
$I(x_i)$ digital input image
$k_b(x_i)$ blur kernel
$N(x_i)$ noise level
$R(x_i)$ input region for determining at least one of the signal level, the noise level and the signal-to-noise ratio
$R_{reg}(x_i)$ regularization function
$S(x_i)$ signal level
$SNR(x_i)$ signal-to-noise ratio
$SNR_{max}$ (predetermined) upper SNR threshold value
$SNR_{min}$ (predetermined) lower SNR threshold value
$V(x_i)$ functional derivative of regularization function
$x_i$ voxel
$\mathbb{D}$ derivative operator
$\mathbb{E}$ mean of an array
a, b, c, n, x, y coordinates, variables
$\beta(x_i)$ noise component of the deconvolution
$\beta_{max}$ (predetermined) maximum noise value
$\beta_{min}$ (predetermined) minimum noise value
$\Omega$ region of the input image, in which an operation is carried out

The invention claimed is:

1. A method for a deconvolution of a digital input image $(I(x_i))$ having a plurality of input voxels $(x_i)$, in particular a digital input image obtained from a medical observation device, such as a microscope or endoscope and/or using fluorescence, the method comprising:

computing a local signal-to-noise ratio $(SNR(x_i))$ within an input region $(R(x_i))$ of the digital input image, the input region consisting of a subset of the plurality of input voxels of the digital input image and surrounding the current input voxel, and computing a noise component (β(SNR)) from the local signal-to-noise ratio, the noise component representing image noise ($n$ ([h*f]($x_i$), n($x_i$))) in the deconvolution, wherein the noise component is limited to a predetermined minimum noise value ($β_{min}$) for a local signal-to-noise ratio above a predetermined upper SNR threshold value ($SNR_{max}$) and is limited to a predetermined maximum noise value ($β_{max}$) for a local signal-to-noise ratio below a predetermined lower SNR threshold value ($SNR_{min}$).

2. The method according to claim 1, wherein the step of computing the local signal-to-noise ratio (SNR) includes computing a local signal level (S($x_i$)) in the input region (R($x_i$)) and a local noise level (N($x_i$)) in the input region (R($x_i$)), and wherein the step of computing the noise level includes computing at least one summed-area table for at least one contiguous region of input voxels ($x_i$).

3. The method according to claim 2, wherein the step of computing the at least one summed-area table includes the step of computing the at least one summed-area table in a parallel manner using a prefix sum.

4. The method according to claim 2, wherein computing the local noise level (N) includes computing a variance of the digital input image (I($x_i$)) using at least one summed-area table.

5. The method according to claim 4, wherein the variance is computed after applying a linear derivative operator ($\mathbb{D}$) to the input image data (I($x_i$)) to obtain derivative image data (I'($x_i$)).

6. The method according to claim 5, wherein the linear derivative operator ($\mathbb{D}$) is a gradient operator or an edge-detection filter.

7. The method according to claim 1, wherein the step of computing the local signal-to-noise ratio (SNR($x_i$)) includes the step of computing a signal level (S($x_i$)) at an input voxel ($x_i$) in the input region (R($x_i$)), and wherein the step of computing the signal level includes convolving the input image data (I($x_i$)) with a blur kernel ($k_b$($x_i$)).

8. The method according to claim 1, wherein the noise component (β(SNR($x_i$))) is computed as having a gradient $$\left(\frac{d\beta(SNR)}{dSNR}\right),$$

which is smaller at the predetermined upper SNR threshold value ($SNR_{max}$) and/or at the predetermined lower SNR threshold value ($SNR_{min}$) than between the predetermined upper SNR threshold value ($SNR_{max}$) and the predetermined lower SNR threshold value ($SNR_{min}$).

9. The method according to claim 8, wherein the step of computing the noise component (β(SNR)) includes the step of computing a trigonometric function.

10. The method according to claim 1, wherein the deconvolution is a Lucy-Richardson deconvolution.

11. A non-transitory computer readable medium storing a program causing a computer to execute the image processing method according to claim 1.

12. A medical observation apparatus, such as a microscope or endoscope comprising an image processor, the image processor being configured to carry out the method according to claim 1.

13. An image processor for a medical observation apparatus, such as a microscope or endoscope, the image processor comprising:
 a memory configured to store a digital input image (I($x_i$)) comprising a plurality of input voxels ($x_i$), and
 a deconvolution engine configured to compute a deconvolved output image (f($x_i$)) from the plurality of input voxels,
 wherein the deconvolution engine comprises a noise component (β(SNR($x_i$))) which depends on a local signal-to-noise ratio (SNR($x_i$)) at an input voxel, the local signal-to-noise ratio being computed only in an input region (R($x_i$)) consisting of a subset of the plurality of input voxels of the digital input image,
 wherein the image processor contains a predetermined upper SNR threshold value ($SNR_{max}$) and a predetermined lower signal-to-noise threshold value ($SNR_{max}$), and
 wherein the noise component is limited to a predetermined minimum noise value ($β_{min}$) for a local signal-to-noise ration above the predetermined upper SNR threshold value ($SNR_{max}$) and to a predetermined maximum value ($β_{max}$) for a local signal-to-noise ratio below the predetermined lower signal-to-noise threshold value ($SNR_{min}$).

14. The image processor according to claim 13, wherein the image processor comprises a summed-area-table generator, the summed-area-table generator being configured to compute a summed-area table of the digital input image and to compute the local noise level using the summed-area table.

15. A microscope or endoscope comprising the image processor according to claim 13.

* * * * *